(12) United States Patent
Stapf

(10) Patent No.: US 7,087,807 B2
(45) Date of Patent: Aug. 8, 2006

(54) TISSUE TREATMENT DEVICE FOR AN EXTREMITY

(75) Inventor: Donald E. Stapf, Minneapolis, MN (US)

(73) Assignee: Arizant Technologies, LLC, Eden Prairie, MN (US)

( * ) Notice: Subject to any disclaimer, the term of this patent is extended or adjusted under 35 U.S.C. 154(b) by 529 days.

(21) Appl. No.: 10/316,611

(22) Filed: Dec. 10, 2002

(65) Prior Publication Data

US 2003/0120194 A1    Jun. 26, 2003

Related U.S. Application Data

(63) Continuation-in-part of application No. 09/908,152, filed on Jul. 18, 2001, now Pat. No. 6,573,420, which is a continuation of application No. 09/437,388, filed on Nov. 10, 1999, now Pat. No. 6,323,386.

(51) Int. Cl.
*A61F 13/00* (2006.01)

(52) U.S. Cl. .............................. 602/48; 602/41; 602/42

(58) Field of Classification Search ................... 602/2, 602/3, 41–48, 57; 128/888, 889, 882, 893, 128/894
See application file for complete search history.

(56) References Cited

U.S. PATENT DOCUMENTS 2,273,873 A * 2/1942 Klein ......................... 128/888

| 4,178,924 | A  |   | 12/1979 | Baxter |
|---|---|---|---|---|
| 5,407,419 | A  |   | 4/1995 | Kelly et al. |
| 5,605,534 | A  |   | 2/1997 | Hutchison |
| 5,643,183 | A  | * | 7/1997 | Hill ............................. 602/3 |
| 6,186,989 | B1 |   | 2/2001 | Horie |
| 6,323,386 | B1 |   | 11/2001 | Stapf et al. |
| 6,512,158 | B1 | * | 1/2003 | Dobos ......................... 602/41 |

FOREIGN PATENT DOCUMENTS

WO     WO9615745    *  5/1996

* cited by examiner

*Primary Examiner*—Kim M. Lewis
(74) *Attorney, Agent, or Firm*—Incaplaw; Terrance A. Meador

(57) ABSTRACT

A tissue treatment device suitable for use on an extremity or a portion of an extremity, such as a hand or foot, includes a cover formed as a bag, sac, or pouch, and a flexible, absorbent support member. Defined sections of the support member may be removed from the support member to form an opening therein. The support member is for being positioned within the cover to support a portion of the cover off of, and out of contact with, tissue to be treated. The cover has an open end with attachment means disposed thereon for attachment to the extremity or extremity portion that is received in the cover. The support member may be impregnated with a medicament. The removable sections allow formation of an opening that may be customized or adapted to the area of tissue that is to receive treatment. This permits the tissue treatment device to be adapted for use with treatment areas that vary in size, shape, contour, and composition.

39 Claims, 6 Drawing Sheets

TISSUE TREATMENT DEVICE FOR AN EXTREMITY

This application is a continuation-in-part of U.S. patent application Ser. No. 09/908,152, filed Jul. 18, 2001, now U.S. Pat. No. 6,573,420 entitled TISSUE TREATMENT DEVICE FOR A LIMB, which is a continuation of U.S. patent application Ser. No. 09/437,388, filed Nov. 10, 1999, now U.S. Pat. No. 6,323,386, entitled WOUND COVERING FOR A FOOT OR HAND.

FIELD OF THE INVENTION

The invention described herein relates to a tissue treatment device, and in particular, to a tissue treatment device capable of being configured in a clinical setting to provide a cover out of contact with tissue to be treated on an awkwardly shaped body part, such as a foot, or a hand, that is capable of delivering heat to the wound. The invention more particularly relates to a tissue treatment device having a flexible, absorbent support member in a bag-like cover for being positioned near the tissue to be treated. Particularly, the invention concerns such a tissue treatment device having a flexible, absorbent support member that includes defined sections that are removable from the support member to enable the formation of openings in the support member which vary in shape and size.

BACKGROUND OF THE INVENTION

A novel mode of tissue treatment employing a non-contact treatment device is disclosed in U.S. Pat. Nos. 5,817,145; 5,947,914 and 6,093,160, each of which is owned in common with the present application and is hereby incorporated by this reference. The device has a central opening between two surfaces for forming a treatment volume against an area of tissue to be treated when one of the surfaces is disposed against tissue surrounding the area without the opening encompassing a limb. The treatment volume is covered at the surface not contacting tissue in order to control parameters of the ambient environment in the treatment volume that are indicated in the treatment to which the tissue is to be subjected. Some of these parameters are temperature, moisture, and treatment materials such as medicaments. The device is particularly effective in treating wounds and reducing infection.

Typically, such a treatment device includes, in addition to other elements, a support member, an attachment portion, and a bag-like cover.

The support member generally comprises a standoff with an opening. The attachment portion is for acting between a 'skin surface and the standoff to connect and retain the treatment device on the skin of a patient, with the opening aimed at an area to be treated along a line that passes through the area. The cover spans the opening, away from the patient's skin surface. Together the standoff and cover define a treatment volume which projects along the intersecting line onto a patient's skin surface, in a two-dimensional area when the device is mounted to the patient's skin. This device is referred to as a "non-contact" device because, when attached to skin, it surrounds an area where treatment is to be applied in such a way that no portion of the device, save the treatment volume, contacts the area.

A novel mode of treatment for an extremity portion such as a foot or a hand which extends the principles of non-contact treatment is disclosed in applicant's U.S. Pat. No. 6,323,386 B1, WOUND COVERING FOR A FOOT OR HAND, which is owned in common with the present application and is hereby incorporated by this reference. This non-contact device includes a flexible, absorbent support member, an attachment portion, and a cover formed as a bag, sac, or pouch. The support member is for being disposed within the cover to support a portion of the cover off of, and out of contact with, an area of tissue to be treated. The support member includes an opening for being aimed at an area where treatment is to be applied along a line that intersects the area. Once the support member is formed, the size and shape of the opening cannot be changed without cutting the support member. Thus, when such a treatment device is received for use in the clinic, the tissue area where treatment is to be applied may be larger than the opening, or may have a shape not accommodated by the shape of the opening. In addition, there may be multiple adjacent areas where treatment is to be applied which, for one reason or another, need separate treatment volumes but cannot be accommodated by multiple support members. In such cases, one size of opening probably will not fit all needs, and it may be necessary for a variety of such treatment devices to be inventoried in order to realize flexibility in treatment.

A need exists, therefore, for a tissue treatment device for use on extremities or extremity portions such as hands or feet in which a support member can be adapted for various sizes, shapes, and numbers of tissue areas where treatment is to be applied. In particular, it would be desirable for the treatment device to be provided with a support member accommodating of one or more treatment areas of different sizes and shapes.

SUMMARY OF THE INVENTION

The present invention is a treatment device that is particularly well suited to treating tissue on an extremity of a patient, such as the hand or foot. The treatment device is useful, for example, to treat tissue or wounds that commonly occur on a patient's extremities, and are particularly difficult to treat.

The invention is a non-contact tissue treatment device having a cover formed as a bag, sac, or pouch, one or more flexible attachment portions, and at least one flexible, absorbent support member capable of having one or more openings made in it of varying shapes and sizes. In this regard, the support member includes a plurality of defined sections which may be arranged in a pattern. One or more of the sections may be selectively removed to form at least one opening through the support member. The removable sections allow formation of an opening that may be customized or adapted to the area of tissue that is to receive treatment. This permits the tissue treatment device to be adapted for use with treatment areas that vary in size, shape, contour, and composition.

BRIEF DESCRIPTION OF THE DRAWINGS

The various figures depict illustrative and exemplary forms of the tissue treatment device disclosed herein. Throughout the several views, identical reference numbers represent similar or equivalent structures.

DETAILED DESCRIPTION

Figure 1:
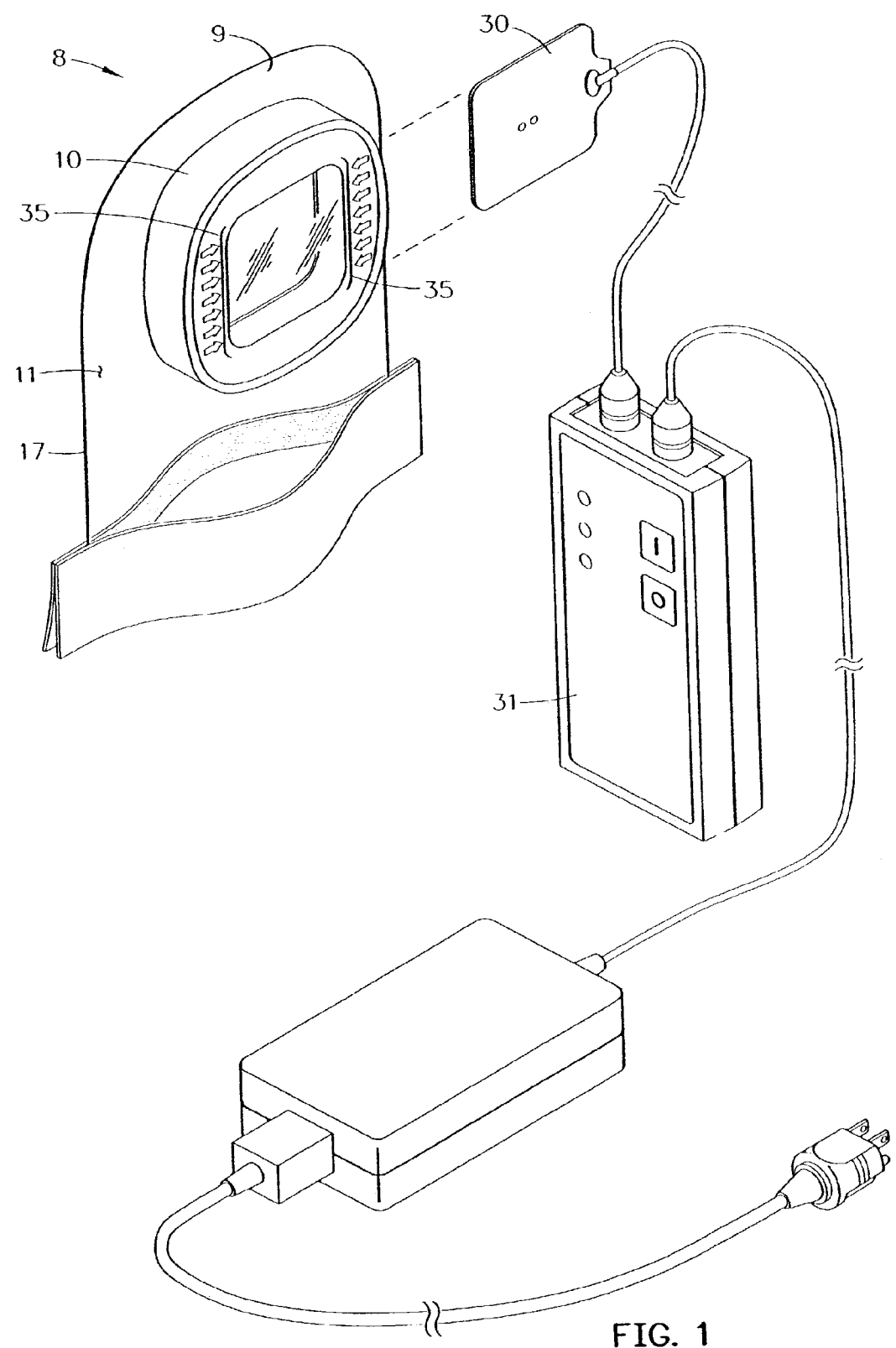
FIG. 1 is a perspective view of one embodiment of the tissue treatment device in combination with a heating system.

Reference is made in this description to tissue treatment and to a tissue treatment area. In this regard, "treatment" is meant in its broadest sense. That is, treatment with the tissue treatment device described herein is the rendering of medical aid to tissue. At the same time, the device also functions to protect tissue which is being treated. A "treatment area" is an area that is defined by an element of the tissue treatment device when the device is deployed for use and that is to receive a treatment provided by the device. The treatment area may include one or more wounds and associated periwound tissue. The treatment area may also be an unwounded area of tissue.

Refer now to FIGS. 1–6 in which embodiments and elements of the present tissue treatment device are illustrated. With respect to FIGS. 1 and 2, there is shown a tissue treatment device 8 that includes a cover 9 formed as a bag, sac, or pouch with an open end, and a flexible absorbent support member 10. The cover may be constructed from two sheets of material, although this construction is merely for illustration and is not intended to limit the construction of the cover 9. In this construction, the cover 9 includes a first sheet 11 and a second sheet 12, each of approximately the same size and shape. The first sheet 11 has an edge 13 and an end 14. The second sheet 12 likewise has an edge 15 and an end 16. A continuous seal 17 is formed between the first and the second edges 13 and 15, joining the two sheets 11 and 12. Together the joined sheets form an enclosure that can fit over an extremity. The enclosure has an open end 14, 16 through which the extremity can extend. Alternatively, the cover 9 may be made from a single sheet of flexible material, or otherwise formed as a single, unseamed member.

Preferably the material of which the cover 9 is made is a flexible, easily worked material that is adaptable to automated manufacturing. Such synthetic materials as flexible plastics are examples. Other materials such as woven and non-woven synthetics, natural, or blended materials are contemplated. The chosen material may be clear or opaque.

Figure 2:
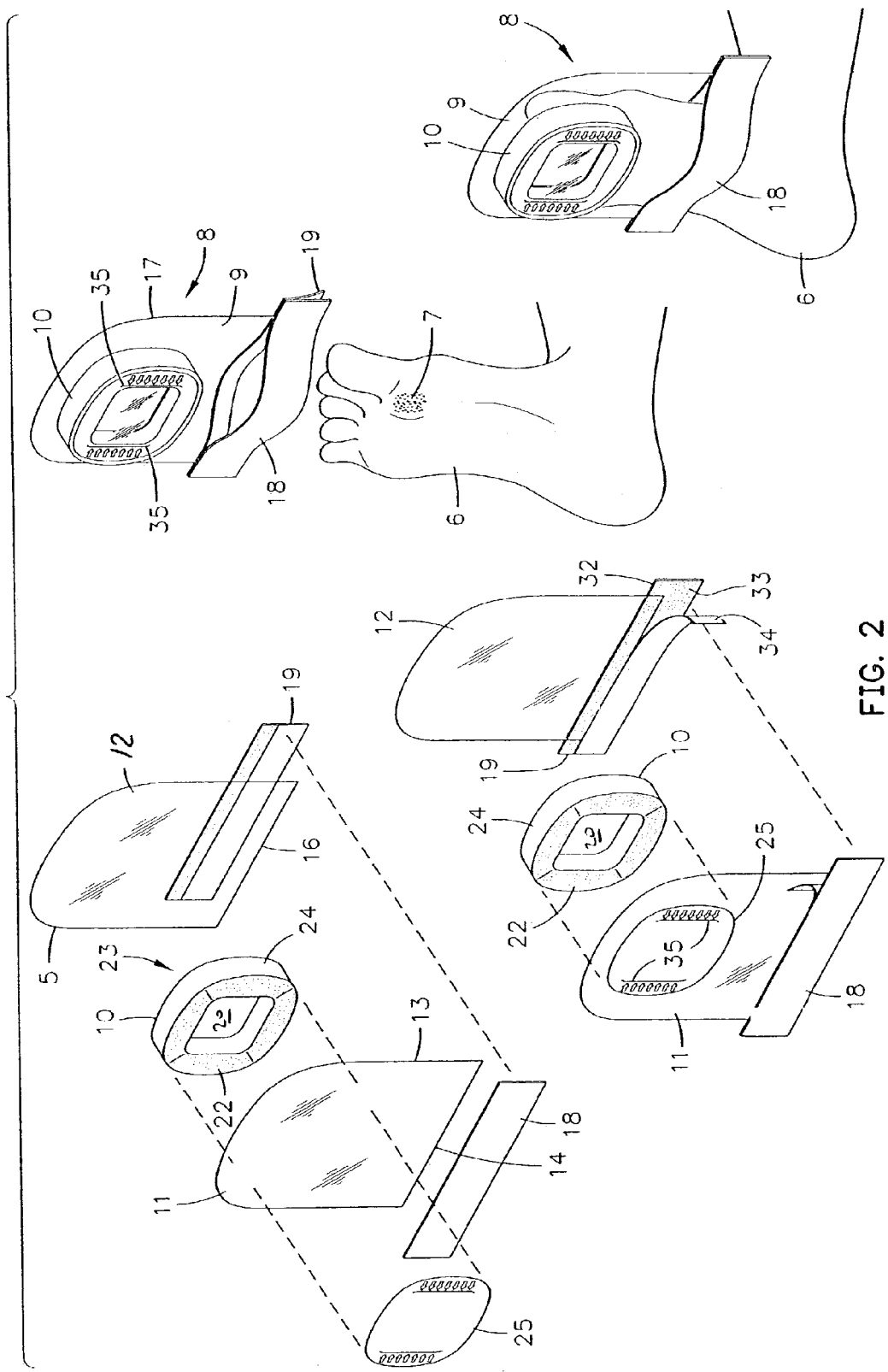
FIG. 2 is an exploded view of one embodiment of the tissue treatment device showing an exemplary construction.
Figure 4:
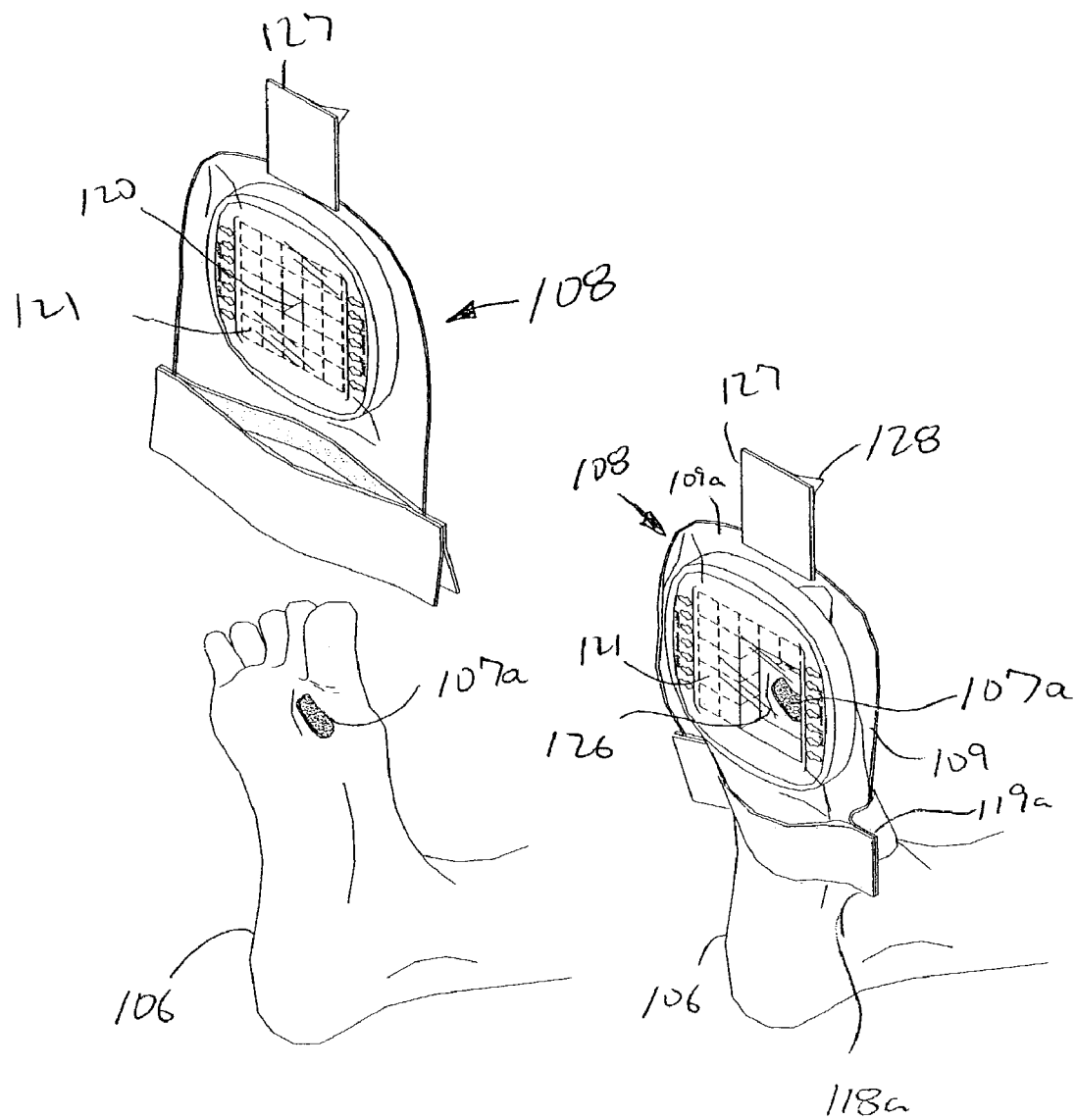
FIGS. 4 and 5 are perspective views of the tissue treatment device of FIG. 3 with an extremity.
Figure 5:
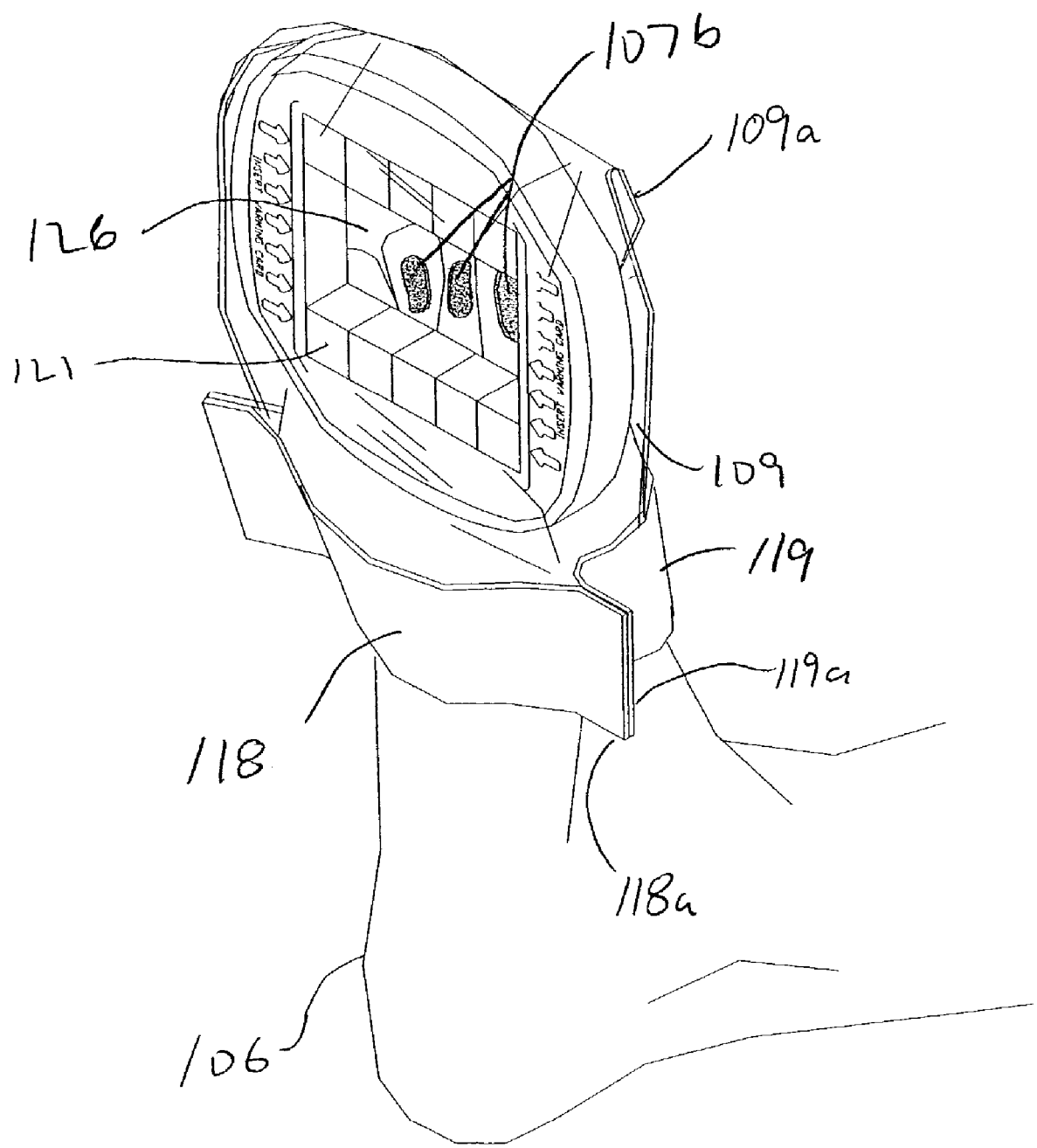

The tissue treatment device 8 further comprises attachment portions 18, 19, which are disposed along the end 14, 16. The attachment portions are used to connect the tissue treatment device 8 to the skin of a patient, sealing the enclosure formed by the cover 9 to a patient's extremity as illustrated in FIG. 2. In FIGS. 2, 4 and 5, the extremity is a foot 6 on the bottom of which is a wound 7.

Referring now to FIG. 2, in the tissue treatment device 8, the attachment portions 18, 19 are integrated unitary assemblies, each preferably having three sections: a foam layer 32, an adhesive film layer 33 on a bottom surface of the foam layer 32, and a release liner 34 covering the adhesive film layer 33. One or more lines of weakness or perforation are provided on the release liner 34 so that its parts may be separated and selectably peeled off of the adhesive film layer 33, thereby exposing the adhesive film layer for attaching to a patient's skin. The foam layer 32 may comprise a naturally open-celled polyurethane foam, and is preferably approximately 1/16" thick. The adhesive film layer 33 may comprise a high MVTR thin film pressure sensitive adhesive (PSA) laminate available as a package under the trade name Mediderm from Bertek. The foam layer 32 is heat bonded to the adhesive film layer 33. The material of which the adhesive film layer is comprised is selected for a combination of adhesion level, permeability, and conformability (stretching and flexing with the skin) to allow prolonged skin contact without complications. An example of an adhesive material is Avery Dennison's med 5666R sold under the tradename Wetstick. The release liner 34 is a white release paper coated with a release agent. An alternative adhesive film is the Mediderm 3701 product. The perforations or slits are made during assembly to aid in the removal of the release liner 34 prior to attachment of a tissue treatment device 8 to a person.

The tissue treatment device 8 further comprises a support member 10 for supporting a portion of the cover 9 off of or away from an area of tissue where treatment is to be applied so as to prevent the cover portion from contacting the tissue (or at least to minimize such contact). Lack of contact between the area and the cover 9 is useful, for example, when a wound to is in the area to be treated. In the embodiment illustrated in FIGS. 1 and 2, the support member 10 is in the shape of a ring. The support member 10 has a central opening 20, a first surface 22, a second surface 23 (not visible in the figures), and an outer perimeter or edge 24. A portion of the inner surface of the cover 9 may be attached to the first surface 22 of the support member 10 as described below. The cover 9 is preferably sized to extend beyond the outer perimeter 24 of the support member 10 as illustrated in FIGS. 1 and 2.

The support member 10 may be formed of a foam material, preferably an absorbent foam. An example of a suitable absorbent foam is a naturally open-celled polyurethane foam that is selected to have favorable characteristics of liquid absorbency, leaking, and resevoiring. Such material is a super absorbent polymer (SAP) filled foam, which may be obtained from Neosorb, Woodbridge, Md. Alternative materials available include products sold under the trade names Aquazone from Foamex, Medisponge from Lendell Manufacturing, and Medical SAP foam from Rynel Ltd. The thickness of the ring-shaped support member 10 is preferably in a range extending from 3/8" to 5/8", with the exact dimension being selected to maintain the cover off of an area of tissue where treatment is to be applied such as an area 7 of skin on the foot 6 whereby, during use, the foam ring 10 can compress and conform without the cover 9 contacting the area 7.

Medicament may be stored in a reservoir of the support member 10, for example, by impregnating the support member 10 itself with medicament, such as an antibiotic, antifungal, or antimicrobrial material. It may also be desirable to impregnate the support member with a deodorant material or a material to release nitric oxide. In any case, the material or materials with which the support member is impregnated, or some one or more constituents of those materials, will passively diffuse over the area in order to control the environment in the treatment volume formed over or against the area.

In use, the support member 10 is positioned on a skin surface portion with the opening aimed at the area 7 along a line which passes through the area. In this manner, the opening is projected onto the skin where the support member is placed, around the area to be treated.

The second surface 23 of the support member 10 may optionally have a moisture barrier film adhered thereto. Such a moisture barrier film allows for smooth contact between the support member 10 and the patient's skin and may prevent maceration of the skin if the support member 10 is wetted by soaking up wound exudate. Optionally, the film may be porous or perforated to allow exudate to be wicked away from the skin and trapped in the foam material of the support member 10. Any moisture barrier film would be suitable, in particular those composed of polyurethane, polyethylene, and the like. The film may be attached to the second surface 23 by means of heat sealing or a ring of adhesive, such as the product sold under the trade name HL-2306-X by H. B. Fuller Adhesive.

The material of the cover 9 preferably is a 2 mil.-thick clear flexible polyurethane film with favorable characteristics selected, but not limited, to include moisture vapor transfer (MVTR), oxygen permeability, and transmission of infrared radiation. A measurable MVTR is particularly desirable when the tissue treatment apparatus is deployed over hands and feet, which sweat profusely. Such material is available sold under the trade name Deerfield 6100S or Omniflex TX1530, the latter providing a preferred surface for adhesion of the stretcher 25. The portion of the inner surface of the cover 9 is attached to the upper surface 22 of the support member 10 by a ring of adhesive comprising a synthetic rubber-base adhesive, such as the product sold under the trade name HL-2306-X. Alternatively, the inner surface of the cover 9 may be heat sealed to the upper surface 22 of the support member 10.

A stretcher layer 25 may be attached to the outer surface of the cover 9 against the support member 10 such that the cover 9 is sandwiched between the stretcher layer 25 and the first surface 22 of the support member 10. The stretcher layer 25 is a 5 mil-thick planar sheet of (preferably) clear, somewhat flexible polyester film having enough stiffness to aid in maintaining planarity. The function of the stretcher layer 25 is to hold the portion of the cover 9 under it taut, much as a "stretcher frame" tautens an artist's canvas. The stretcher layer 25 is attached to the cover 9 by a layer of adhesive comprising a clear flexible polyester carrier film coated on both sides with an aggressive adhesive. The adhesive layer is oriented over the first surface 22 of the support member 10. The stretcher layer 25 further includes a pair of slits 35 that receive a detachable heater 30. With the provision of the slits 35, a pocket is formed between the stretcher layer 25 and the cover 9.

FIG. 1 shows a detachable heater 30 positioned to slide into a slit 35 in the stretcher layer 25 which forms a pocket with the cover 9. When inserted, the heater 30 is supported substantially in a plane or surface above a wound by the support member 10. The heater 30 is generally planar and may be connected to and powered by a portable power supply 31, such as those heaters described in detail in U.S. Pat. Nos. 5,954,680, 5,964,723 and 5,986,163, each of which is owned in common with the present application and are hereby incorporated by this reference. The application of heat may be of particular therapeutic benefit by improving cellular physiologic functions, immune competence, and perfusion in the wound area.

Figure 3:
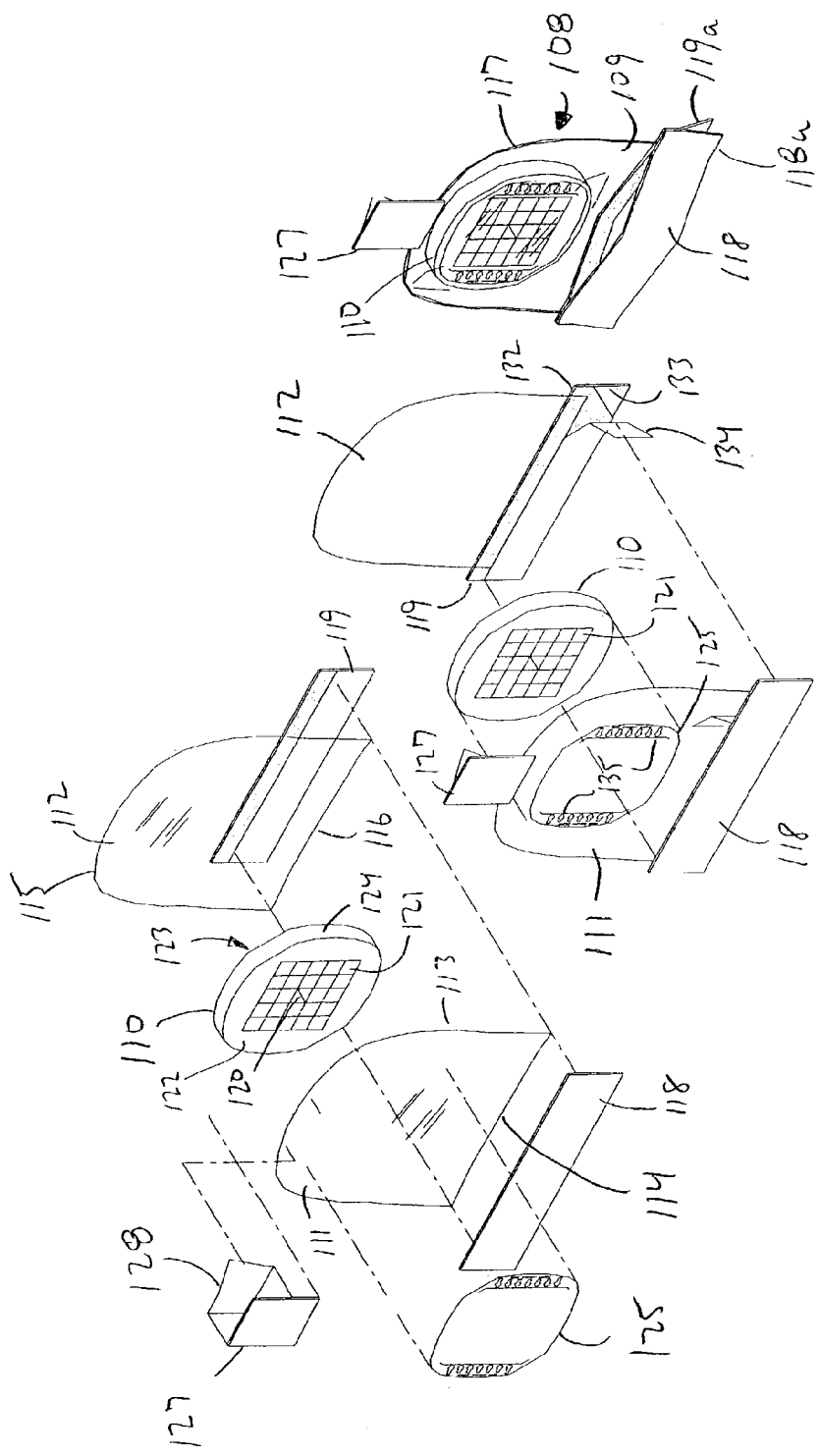
FIG. 3 is an exploded view of another embodiment of the tissue treatment device.

Another embodiment of the present invention is illustrated in FIGS. 3–5, where is shown a tissue treatment device 108 that includes a cover 109 formed as a bag, sac, or pouch, with an open end, and a support member 110. As explained above with reference to FIGS. 1 and 2, the cover may be constructed from two sheets of material, although this construction is merely for illustration and is not intended to so limit the construction of the cover 109. In this construction, the cover 109 includes a first sheet 111 and a second sheet 112, each of approximately the same size and shape. The first sheet 111 has an edge 113 and an end 114. The second sheet 112 likewise has an edge 115 and an end 116. A continuous seal 117 is formed between the first and the second edges 113 and 115, joining the two sheets 111 and 112. Together the joined sheets form an enclosure that can fit over an extremity. Alternatively, the cover 109 may be made from a single sheet of flexible material, or formed as a single member. The enclosure has an open end through which the extremity can extend. Once over the extremity, the enclosure may be sealed around the extremity if desired.

Preferably the material of which the cover 109 is made is a flexible, easily worked material that is adaptable to automated manufacturing. Such synthetic materials as flexible plastics are examples. Other materials such as woven and non-woven synthetics, natural, or blended materials are contemplated. The chosen material may be clear or opaque.

The tissue treatment device 108 further comprises attachment portions 118, 119, which are disposed along the end 114, 116. The attachment portions are used to connect the tissue treatment device 108 to a patient's extremity, as illustrated in FIGS. 4 and 5. In FIGS. 4 and 5, the extremity is a foot 106 on the bottom of which one or more wounds 107*a* and 107*b* are illustrated.

Referring now to FIG. 3, in the tissue treatment device 108, the attachment portions 118, 119 may be made of adhesive strips, such as tape. In the figures shown, the tape is a integrated unitary assembly having three sections: a foam layer 132, an adhesive film layer 133 on a bottom surface of the foam layer 132, and a release liner 134 covering the adhesive film layer 133. The foam layer 132 may comprise a naturally open-celled polyurethane foam. One or more lines of weakness or perforation are provided on the release liner 134 so that its parts may be separated and selectably peeled off of the adhesive film layer 133, thereby exposing the adhesive film layer for attaching to a patient's skin. The perforations or slits are made during assembly to aid in the removal of the release liner 134 prior to attachment of a tissue treatment device 108 to a person.

When the tissue treatment device 108 is put over the patient's extremity, the open end of the cover may need to be sealed around the extremity. As shown in FIGS. 4 and 5, once the tissue treatment device 108 is in position, the attachment portions 118 and 119 are attached to the extremity, in this case the foot 106. Then the end portions 118*a* and 199*a* of the attachment portions 118 and 119 are pinched together to seal the tissue treatment device 108 over the extremity 106 and help keep it in place.

The tissue treatment device 108 disclosed herein includes a support member 110 for supporting a portion of the cover 109 off of or away from the area of tissue where treatment is to be applied so as to prevent the cover portion from contacting the area (or at least to minimize such contact). In the embodiments illustrated in FIGS. 3–6, the support members 110 and 210 are in the shape of a disc, although this is not meant as a limitation. The support member 110 may have an initially closed area composed of a plurality of removable sections 121 which may be selectively removed to form one or more openings in the support member 110. In FIGS. 3–5, these sections are formed as regular cubes disposed in a two-dimensional matrix from which they may be removed. Such forms and shapes are not necessary to the invention. For example the removable sections may be formed as concentric rings as taught in U.S. Pat. No. 6,143,945, which has been incorporated herein by reference. In FIG. 3, one of the removable sections 121 is shown removed, thereby forming an initial opening 120. In addition, the support member 110 has a first surface 122, a second surface 123 (not visible in the figures), and an outer perimeter or edge 124. A portion of the inner surface of the cover 109 may be attached to the first surface 122 of the support member 110 as described below, against an opening formed in the support member, to form a treatment volume 126 therewith. The cover 109 is preferably sized to extend beyond the outer perimeter 124 of the support member 110 as illustrated in FIGS. 3–5. The removable sections 121 may be defined by a sharp-edged form brought against one of the surfaces 122, 123 to cut part way into the support member 110, without penetrating it, or by cutters that penetrate completely portions of the support member leaving some portions uncut. The sections can also be formed by molding the support member in a frame.

An opening may be formed in the support member 110 that is adjustable in size and shape, so that it may be tailored to fit one or more treatment areas that vary in size or shape. In this regard, one or more of the removable sections 121 may be removed to create an opening. For example, shown in FIG. 4, approximately 11 removable sections 121 are removed from the lower right side of the initial opening 120 to accommodate a wound 107a. FIG. 5 shows another example where approximately 14 removable sections 121 comprising the center three rows of the ring-shaped support member 110 are removed to accommodate three wounds 107b. As can be appreciated, there are openings of many other shapes, sizes and configurations that can be made by removing one or more of the removable sections 121.

The support member 110 is preferably made of a foam material, preferably an absorbent foam. An example of a suitable absorbent foam is a naturally open-celled polyurethane foam that is selected to have favorable characteristics of liquid absorbency, wicking, and resevoiring, as described in reference to support member 10. Medicament may be stored in a reservoir of the support member 10, for example, by impregnating, infusing, spraying or disposing on the support member 10 itself with medicament, such as an antibiotic, antifungal, or antimicrobrial material. It may also be desirable to impregnate, infuse, spray or dispose on the support member with a deodorant material or a material to release nitric oxide. In any case, the material or materials with which the support member is impregnated, or some one or more constituents of those materials, will passively diffuse over the area in order to control the environment in the treatment volume formed over or against the area. The application of heat by means of a heater such as the heater 30 may assist the diffusion or activity of the medicaments. There also may be some type of containment system, such as a removable cover, bag or tape, that prevents the materials from dispersing or diffusing from the foam prior to use. The thickness of the ring-shaped support member 110 is dimensioned to maintain the cover off of a treatment area 107 whereby, during use, the support member 110 can compress and conform without the cover 109 contacting the area.

In use, the support member 110 is positioned on a skin surface portion with the opening aimed at the treatment area 107 along a line which passes through the area. In this manner, the opening is projected onto the skin where the support member is placed, around the area to be treated.

The second surface 123 of the ring-shaped support member 110 may optionally have a moisture barrier film adhered thereto. Such a moisture barrier film allows for smooth contact between the support member 110 and the patient's skin and may prevent maceration of the skin if the support member 110 is wetted by soaking up wound exudate. Optionally, the film may be porous or perforated to allow exudate to be wicked away from the skin and trapped in the foam material of the support member 110. Any moisture barrier film would be suitable, in particular those composed of polyurethane, polyethylene, and the like. The film may be attached to the second surface 123 by means of heat sealing or a ring of adhesive.

The material of the cover 109 is the same as that of cover 9, which is preferably a clear flexible polyurethane film with favorable characteristics selected, but not limited, to include moisture vapor transfer (MVTR), oxygen permeability, and transmission of infrared radiation. A measurable MVTR is particularly desirable when the tissue treatment apparatus is deployed over hands and feet, which sweat profusely. The portion of the inner surface of the cover 109 is attached to the upper surface 122 of the support member 110 by a ring of adhesive.

A stretcher layer 125 may be attached to the outer surface of the cover 109 against the support member 110 such that the cover is sandwiched between the stretcher layer 125 and the first surface 122 of the support member 110. The stretcher layer 125 is preferably clear and somewhat flexible film having enough stiffness to aid in maintaining planarity. The function of the stretcher layer 125 is to hold the portion of the cover 109 under it taut, much as a "stretcher frame" tautens an artist's canvas. The stretcher layer 125 is attached to the cover 109 over the treatment volume 126 by a layer of adhesive and a pocket is formed between the stretcher layer 125 and the cover 109. The stretcher layer 125 further includes one or more slits 135 to access the pocket. The pocket can be used for different applications, such as holding a detachable heater 30 (as described and shown in conjunction with FIG. 1).

Along a top portion of the cover 109 a short adhesive strip 127 may be placed. The strip 127 may have a release liner 128 covering the adhesive layer. Once the cover 109 is placed over the extremity 106, there may be some excess cover or film 109a at the closed end of the cover 109. If there is, it may be gathered by the adhesive strip 127. In this regard, the release liner 128 is removed and the excess film 109a is folded over the extremity 106 and held to the cover 109 by the adhesive strip 127, as shown in FIGS. 4 and 5.

Figure 6:
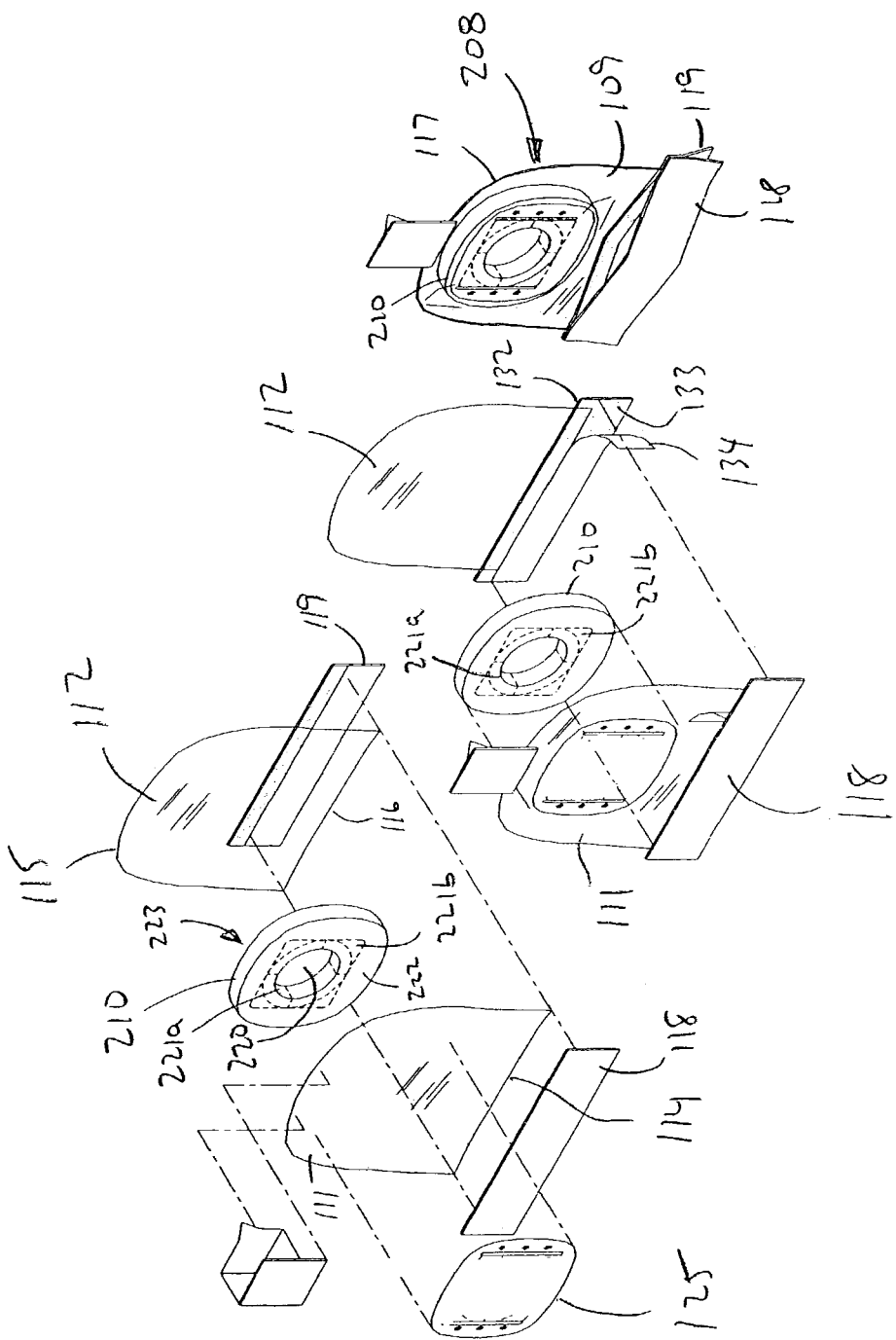
FIG. 6 is an exploded view of still another embodiment of the tissue treatment device.

Another embodiment of a tissue treatment device 208 is illustrated in FIG. 6, which is similar in design and construction to the tissue treatment device 108, with similar components using similar reference numbers. FIG. 6 shows an exploded view of the tissue treatment device 208 for use on an extremity including cover 109, described above in connection with the tissue treatment device 108.

The tissue treatment device 208 further comprises a support member 210, which is similar to the support member 110 in design, construction and function. The support member 210 has an opening 220, a plurality of removable sections 221 around the central opening 220, a first surface 222 and a second surface 223 (not visible in the figures). The support member 210 is made of a flexible foam material and may have treatment materials stored in a reservoir, such as described above for the support member 110. The inner surface of the support member 210 may optionally be all or partially modified by having a moisture barrier film adhered thereto, as described for the support member 110 above.

The removable sections that surround the opening 220 in the support member 210 are for adjusting the size and shape of the opening, so that it may be tailored to fit the size and shape of different treatment areas. One or more of the removable sections 221 may be removed to create a larger or shaped opening 220. Proximate the central opening 220 is an annulus-shaped removable section 221a that is removable in four sections. Proximate the removable section 221a are four corner removable sections 221b. As can be understood, one or more of the removable sections 221a and 221b may be removed to create a larger or shaped opening 220. For example, if all the removable sections 221a, 221b were removed, the support member 210 would be very similar looking to the support member 10 shown in FIG. 2, having a rectangular center opening.

A portion of the inner surface 222 is attached to the cover 109, generally in the same manner and using similar materials as described above for support member 110, forming a similar treatment volume. The second surface 223 of the ring-shaped support member 210 may optionally have a moisture barrier film adhered thereto, the same as described above for support member 110.

The following describes use of the tissue treatment devices disclosed. Presume that the tissue to which treatment to be applied is, or contains, a wound. In this case, the tissue to be treated is cleaned, including the area around the wound (the "periwound"). A skin protector or sealant may be applied to the periwound area to protect it from exudates and adhesives. The wound is measured to determine the size opening required in the support member. It is preferred that the edges of the opening be near but not touching the wound. If enlargement is needed, one or more of the plurality of removable sections or segments of the support member are removed to create an appropriately sized and shaped opening. The cover is slid over the extremity and positioned so the wound can be seen through the window. With the wound in the window, the adhesive liner is removed on the window side of the wound cover and the adhesive is pressed against the skin. The adhesive should be smooth to help it stick to the skin and make an adequate seal. Then the other adhesive liner is removed and the adhesive is pressed firmly against the skin. The ends of the adhesive strips are pinched together to seal the cover and help keep in it place. If there is excess film at the top of the cover, a short adhesive strip is used to adjust the fit. The liner is removed from the short adhesive strip, the excess film is folded over and the short adhesive strip is attached to the cover. The tissue treatment device is now in place. The heater or warming card may be activated. In addition, medicaments that may be stored in the support member may now be released.

While the invention has been illustrated by means of specific embodiments and examples of use, it will be evident to those skilled in the art that many variations and modifications may be made therein without deviating from the scope and spirit of the invention. However, it is to be understood that the scope of the present invention is to be limited only by the appended claims.

The invention claimed is:

1. A tissue treatment device, comprising:
   a bag-like cover with an open end;
   an absorbent support member for being positioned within the cover;
   a plurality of removable sections in the support member for being removed to provide an opening through the support member;
   a medicament stored in the support member for being released into the opening;
   a layer of material joined to the outer surface of the cover;
   a pocket between the layer of material and the cover; and
   at least one slit in the layer which opens into the pocket.

2. The tissue treatment device of claim 1, wherein the medicament is selected from the group consisting of an antibiotic material, an antifungal material, an antimicrobial material, a deodorant material and nitric oxide.

3. The tissue treatment device of claim 1, wherein the support member comprises a ring-shaped foam member.

4. The tissue treatment device of claim 1, wherein the support member comprises a rectangular foam member.

5. The tissue treatment device of claim 1 further comprising one or more attachment portions disposed along the open end.

6. The tissue treatment device of claim 1, wherein the support member has a first surface and a second surface, the cover has an inner surface and an outer surface and the first surface of the support member has means for attachment to the inner surface of the cover.

7. The tissue treatment device of claim 1 further comprising a heater for being disposed in the pocket.

8. The tissue treatment device of claim 7 further comprising a power supply for being connected to the heater.

9. A tissue treatment device, comprising:
   a bag-like cover with an open end;
   a support member with a central opening for being positioned within the cover;
   a plurality of removable sections in the support member, surrounding the central opening;
   the support member having a first surface and a second surface;
   the cover having an inner surface;
   the first surface of the support member having means for attachment to the inner surface of the cover; and
   a flexible, non-adhesive material attached to the second surface of the support member.

10. The tissue treatment device of claim 9, wherein the support member has the shape of a ring.

11. The tissue treatment device of claim 10, wherein the support member is made of an absorbent foam material.

12. The tissue treatment device of claim 11 further comprising a treatment material disposed in the foam material for being released into the opening to treat tissue.

13. The tissue treatment device of claim 12, wherein the treatment material is selected from the group consisting of an antibiotic material, an antifungal material, an antimicrobial material, a deodorant material and nitric oxide.

14. The tissue treatment device of claim 9 further comprising a moisture barrier film attached to the second surface of the support member.

15. The tissue treatment device of claim 14, wherein the moisture barrier film is porous.

16. The tissue treatment device of claim 9 further comprising a layer of material disposed against an outer surface of the cover.

17. The tissue treatment device of claim 16 further comprising:
   a pocket between layer of material and the cover; and
   at least one slit opening into the pocket.

18. The tissue treatment device of claim 17 further comprising a heater for being disposed in the pocket.

19. The tissue treatment device of claim 18 further comprising a power supply for being connected to the heater.

20. The tissue treatment device of claim 9 further comprising one or more attachment portions disposed along the open end.

21. The tissue treatment device of claim 20, wherein the one or more attachment portions each includes an adhesive material.

22. The tissue treatment device of claim 21, wherein the one or more attachment portions each includes a backing layer of foam material, the adhesive material carried on a surface of the foam material.

23. The tissue treatment device of claim 22, wherein the one or more attachment portions include a release layer carried on the adhesive material.

24. The tissue treatment device of claim 23, wherein the release layer has one or more lines of weakness for permitting a portion of the release layer to be removed from the adhesive material.

25. The tissue treatment device of claim 20, wherein the one or more attachment portions is capable of sealing the cover to the extremity forming a sealed enclosure.

26. The tissue treatment device of claim 9, wherein the cover is formed from a single sheet of flexible material.

27. The tissue treatment device of claim 9, the cover comprising two opposing sheets of material joined along a portion of their respective edges.

28. The tissue treatment device of claim 27, each sheet comprising a 2 mil. thick film of polyurethane.

29. A method for treating tissue on a patient's extremity with a tissue treatment device, the tissue treatment device including:
 a bag-like cover with an open end;
 one or more attachment portions disposed along the open end; and
 an absorbent support member having a plurality of removable sections;
the method comprising:
 removing one or more of the plurality of removable sections to form an opening in the support member;
 with the support member received in the bag-like cover, placing the tissue treatment device over the patient's extremity;
 positioning the opening over the tissue to be treated; and
 attaching the tissue treatment device to the patient's extremity with one or more attachment portions.

30. The method of claim 29, further including storing a treatment material in the support member.

31. The method of claim 30 further comprising releasing the treatment material, or constituents of the treatment material, from the support member through the opening.

32. The method of claim 31, wherein the treatment material is selected from the group consisting of an antibiotic material, an antifungal material, an antimicrobrial material, a deodorant material and nitric oxide.

33. The method of claim 31, wherein storing a treatment material includes impregnating the absorbent support member with a medicament.

34. The method of claim 29, wherein attaching the tissue treatment device includes sealing the tissue treatment device to the patient's extremity.

35. The method of claim 29, wherein the tissue treatment device further includes:
 an outer surface on the cover;
 a layer of material attached to the outer surface of the cover;
 at least one slit in the layer of material.

36. The method of claim 35 further comprising inserting a heater through the slit.

37. The method of claim 36 further comprising operating the heater.

38. The method of claim 29 further including releasing a treatment material, or constituents of the treatment material, from the support member through the opening.

39. The method of claim 38, wherein the treatment material is selected from the group consisting of an antibiotic material, an antifungal material, an antimicrobrial material, a deodorant material and nitric oxide.

* * * * *